United States Patent
Buhr et al.

(10) Patent No.: US 6,476,205 B1
(45) Date of Patent: Nov. 5, 2002

(54) 2' MODIFIED OLIGONUCLEOTIDES

(75) Inventors: Chris A. Buhr, Daly City; Mark Matteucci, Burkingue, both of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/131,647

(22) Filed: Aug. 10, 1998

Related U.S. Application Data

(63) Continuation of application No. 08/467,422, filed on Jun. 6, 1995, now Pat. No. 5,792,847, which is a continuation of application No. 08/240,508, filed on May 10, 1994, now Pat. No. 5,466,786, which is a continuation of application No. 07/425,857, filed on Oct. 24, 1989, now abandoned.

(51) Int. Cl.⁷ .......................... C07H 21/02; C07H 21/04
(52) U.S. Cl. .................. 536/23.1; 536/16.8; 536/26.26; 536/26.7; 536/26.8; 536/27.21; 536/28.1; 536/22.1; 536/25.3; 536/25.32; 536/25.34
(58) Field of Search ............................. 536/16.8, 26.26, 536/26.6, 26.7, 26.8, 27.21, 28.1, 28.54, 28.53, 28.5, 23.1; 514/45, 46, 47, 48, 49, 50, 51

(56) References Cited

U.S. PATENT DOCUMENTS

| | | | |
|---|---|---|---|
| 4,458,066 A | | 7/1984 | Caruthers et al. |
| 4,476,301 A | | 10/1984 | Imbach et al. |
| 4,711,955 A | | 12/1987 | Ward et al. |
| 4,828,979 A | | 5/1989 | Klevan et al. |
| 4,924,624 A | | 5/1990 | Suhadolnik et al. |
| 4,981,957 A | | 1/1991 | Lebleu et al. |
| 5,013,830 A | * | 5/1991 | Ohtsuka et al. |
| 5,109,126 A | | 4/1992 | Agrawal et al. |
| 5,264,423 A | | 11/1993 | Cohen et al. |
| 5,466,786 A | * | 11/1995 | Buhr et al. |
| 5,792,847 A | * | 8/1998 | Buhr et al. |

FOREIGN PATENT DOCUMENTS

| | | | |
|---|---|---|---|
| EP | 0.267.996 A1 | | 11/1986 |
| EP | 0267996 A1 | * | 11/1986 |
| EP | 0 269 574 | | 6/1988 |
| EP | 0 339 842 A3 | | 11/1989 |
| EP | 0 679 657 A2 | | 11/1995 |
| EP | 0 339 842 B1 | | 11/1996 |
| WO | WO 86/05518 | | 9/1986 |
| WO | WO 89/05853 | | 6/1989 |

OTHER PUBLICATIONS

Shibahara, S., et al., "Inhibition of human immunodeficiency virus (HIV–1) replication by synthetic oligo–RNA derivatives," *Nucleic Acids Research*, 1989, 17(1), 239–252.

Alderfer et al., "Comparative Studies on Homopolymers of Adenylic Acid Possessing Different C–2' Substituents of the Furanose. Poly(deoxyriboadenylic acid), Poly(riboadenylic acid), Poly(2'–0–methyladenylic acid), and Poly(2'–0–ethyladenylic acid)", 13(8):1615–1622, Biochem, 1974.

Andrus et al., "Novel Activating and Capping Reagents for Improved Hydrogen–Phosphonate DNA Synthesis", 29(8):861–864, Tet Lett, 1988.

Arnott et al., "Structures for the Polynucleotide Complexes Poly(dA) •Poly(dT) and Poly(dT) •Poly(dA) •Poly(dT)", 88:509–521, J Mol Biol, 1974.

Baum, R.M., "Mechanism of Sequence–Specific DNA Recognition Elucidated", pp. 20–26, C&E News, Jan. 4, 1988.

Bobst et al., "Role of the Ribose 2'–Hydroxyl Groups for the Stabilization of the Ordered Structures of Ribonucleic Acid", 91(16):4603–4604, J Am Chem Soc, Jul. 30, 1969.

Chavis et al., "Synthesis of 2',3'–Differentiated Ribonucleosides via Glycosylation Reactions with 2–O–Me or 2–O–TBDMS Ribofuranose Derivatives. 1. Pyrimidine Series", 47:202–206, J Org Chem, 1982.

Chladek et al., "Oligonucleotidic Compounds. VIII. Synthesis of Adenyl (5' –>3')–Uridine, Adenylyl–(5' –>3')–Cytidine, Guanylyl–(5' –>3')–Uridine, Guanylyl–(5' –>3')–Cytidine, Cytidylyl–(5'–>3')–Cytidine, Adenylyl–(5' –>3')–Uridylyl–(5' –>3') . . . ", 29:214–233, Collect Czech Chem Commun, 1964.

Chladek et al., "Oligonucleotidic Compounds. XII. Synthesis of Cytidylyl–(3' –>5')–Cytidylyl–(3' –>5')–Adenosine (CpCpA), an Acceptor Sequence of Soluble Ribonucleic Acid", 31:1785–1802, Collect Czech Chem Commun. 1966.

Chollet et al., "DNA containing the base analogue 2–aminoadenine: preparation, use as hybridization probes and cleavage by restriction endonucleases", 16(1):305–317, Nuc Acids Res, 1988.

Clontech, "Advertisement", 16(22), Nuc Acids Res, Nov. 25, 1988.

Cooney et al., "Site–Specific Oligonucleotide Binding Represses Transcription of the Human c–myc Gene In Vitro", 241:456–459, Science, 1988.

Cummins et al., "Characterization of fully 2'–modified oligoribonucleotide hetero– and homoduplex hybridization and nuclease sensitivity", 23(11):2019–2024, Nuc Acids Res, 1995.

Dervan, P.B., "Sequence Specific Recognition of Double Helical DNA. A Synthetic Approach", 2:49–64, Nucleic Acids and Molecular Biology (Eckstein & Lilley, Eds.), 1988.

(List continued on next page.)

*Primary Examiner*—James O. Wilson
(74) *Attorney, Agent, or Firm*—Woodcock Washburn LLP

(57) ABSTRACT

Oligomers which have substituents on the 2' position are resistant to oligonucleases and furthermore can be derivatized to deliver reagents or drugs, to carry label, or to provide other properties.

6 Claims, No Drawings

OTHER PUBLICATIONS

Divakar et al., "Reaction Between 2,2'–Anhydro–1–beta–o–arabinofuranosyluracil and Thiolate Ions", pp. 1625–1628, J Chem Soc Perkin Trans I, 1982.

François et al., "Sequence–specific recognition of the major groove of DNA by oligodeoxynucleotides via triple helix formation. Footprinting studies", 16:11431–11440, Nuc Acids Res, 1988.

Froehler et al., "Deoxynucleoside H–Phosphonate Diester Intermediates in the Synthesis of Internucleotide Phosphate Analogues", 27:5575–5578, Tet Lett, 1986.

Froehler et al., "The Use of Nucleoside H–Phosphonates in the Synthesis of Deoxyoligonucleotides", 6:287–291, Nucls & Nuclt, 1987.

Fukukawa et al., "Studies on the Synthesis of Pyrimidine Deoxynucleosides. I. Synthesis of 2',3'–Dideoxyuridine and 1–(3–Ethylthio–3–deoxy–beta–D–xylofuranosyl)uracil", 18:554–560, Chem Pharm Bull, 1970.

Fukukawa et al., "Synthesis of 2'(R)–Substituted Neplanocin A's (Nucleosides and Nucleotides. XXXVII)", 29(2):597–600, Chem Pharm Bull, 1981.

Griffin et al., "Recognition of Thymine–Adenine Base Pairs by Guanine in a Pyrimidine Triple Helix Motif", 245:967–971, Science, 1989.

Griffin et al., "Some Observations Relating to Acyl Mobility in Aminoacyl Soluble Ribonucleic Acids", 5(11):3638–3649, Biochem, Nov. 1966.

Hobbs et al., "Polynucleotides Containing 2'–Chloro–2'–deoxyribose", 11(23):4336–4344, Biochem, 1972.

Hobbs et al., "Polynucleotides Containing 2'–Amino–2'–deoxyribose and 2'–Azido–2'–deoxyribose", 12:5138–5145, Biochem, 1973.

Hobbs et al., "Poly 2'–Deoxy–2'–Aminouridylic Acid", 46(4):1509–1515, Biochem Biophys Res Comm, 1972.

Inoue et al., "Synthesis and hybridization studies on two complementary nona(2'–methyl)ribonucleotides", 15:6131–6148, Nuc Acids Res, 1987.

Inoue et al., "Synthesis and properties of novel nucleic acid probes", 16:165–169, Nuc Acids Res, 1985.

Inoue et al., "Sequence–dependent hydrolysis of RNA using modified oligonucleotide splints and RNase H", 215(2):327–330, FEBS, May 1987.

Iribarren et al., "2'–O–Alkyl oligoribonucleotides as antisense probes", 87:7747–7751, Proc Natl Acad Sci, Oct. 1990.

Izant et al., "Constitutive and Conditional Suppression of Exogenous and Endogenous Genes by Anti–Sense RNA", 229:345–352, Science, 1985.

Janik et al., "Synthesis and Properties of Poly 2' – Fluoro–2'–Deoxyuridylic Acid", 46(3):1153–1160, Biochem Biophys Res Comm, 1972.

Jencks, William P., "Preparation and Properties of Acyl Adenylates", 6:762–766, Methods in Enzymology, 1959.

Johnston, G. A. R., "Acetylation of Nucleosides and Acetyl Migration", 24:6987–6993, Tetrahedron, 1968.

Kaufmann et al., "Phosphorolysis of Aminoacyl–tRNA by Polynucleotide Phosphorylase from Escherichia coli", 12:85–92, Eur J Biochem, 1970.

Kaufmann et al., "Monofunctional Substrates of Polynucleotide Phosphorylase", 24:4–11, Eur J Biochem, 1971.

Keller et al., "Synthesis and hybridization properties of oligonucleotides containing 2'–O–modified ribonucleotides", 21(19):4499–4505, Nuc Acids Res, 1993.

Khurshid et al., "The Unique Conformational Stability Of Poly 2'–O–Ethyladenylic Acid", 28(1):25–28, FEBS, Nov. 1972.

Kielanowska et al., "Preparation and Properties of Poly 2'–O–Ethylcytidylic Acid", 3(3):817–824, Nuc Acids Res, Mar. 1976.

Kusmierek et al., "Alkylation of Cytidine–5'–Phosphate: Mechanisms of Alkylation, Influence of O'–Alkylation on Susceptibility of Pyrimidine Nucleotides to Some Nucleolytic Enzymes, and Synthesis of 2' O–Alkyl Polynucleotides", 20(4):365–381, Acta Biochimica Polonica, 1973.

Lamond et al., "Antisense oligonucleotides made of 2' O–alkylRNA: their properties and applications in RNA biochemistry", 325(1,2):123–127, FEBS, Jun. 1993.

Lapidot et al., "Studies on Polynucleotides. XXVIII. The Specific synthesis of C3,–C5,–Linked Ribooligonucleotides (4). The Stepwise Synthesis of Uridylyl–(3' –>5')–adenylyl–(3' –> 5')–uridylyl–(3' –> 5')–uridine", 85:3852–3857, J Am Chem Soc, 1963.

Larock, Richard C., "Comprehensive Organic Transformations: a guide to functional group preparations", 353:358–362, , 1989.

Lesnik et al., "Oligodeoxynucleotides Containing 2'–0–Modified Adenosine: Synthesis and Effects on Stability of DNA:RNA Duplexes", 32:7832–7838, Biochem, 1993.

Letsinger et al., "Cationic Oligonucleotides", 110:4470–4471, J Am Chem Soc, 1988.

Mackey et al., "New Approach to the Synthesis of Polyribonucleotides of Defined Sequence", 233:551–553, Nature, Oct. 22, 1971.

Maher et al., "Inhibition of DNA Binding Proteins by Oligonucleotide–Directed Triple Helix Formation", 245:725–730, Science, 1989.

Maniatis et al., "Molecular Cloning—A Laboratory Manual", pp. 324–325, Molecular Cloning—A Laboratory Manual, 1982.

Maniatis et al., "Molecular Cloning—A Laboratory Manual", pp. 326:328; 382–389, Molecular Cloning—A Laboratory Manual, 1982.

Maniatis et al., "Molecular Cloning—A Laboratory Manual", pp. 458–460, Molecular Cloning—A Laboratory Manual, 1982.

Matsuda et al., "Alkyl Addition Reaction of Pyrimidine 2'Ketonucleosides: Synthesis of 2'–Branched–Chain Sugar Pyrimidine Nucleosides (Nucleosides and Nucleotides. LXXXI)", 36(3):945–953, Chem Pharm Bull, 1988.

McLaughlin et al., "Chemical Studies on Amino Acid Acceptor Ribonucleic Acids. IV. Position of the Amino Acid Residue in Aminoacyl s–RNA: Chemical Approach", 4(7):1442–1447, Biochem, Jul. 1965.

Mukai et al., "A new method for the unidirectional deletion of DNA with Bal 31 nuclease using 2'–O–MeRNA–DNA chimeric adaptors", 19:117–120, Nuc Acids Res, 1988.

Ogilvie et al., "Total chemical synthesis of a 77 –nucleotide–long RNA sequence having methionine–acceptance activity", 85:5764–5768, Proc Natl Acad Sci, Aug. 1988.

Pike et al., "Mixed Alkylation (Methylation and Ethylation) of Adenosine by Diazoethane in Aqueous 1,2–Dimethoxyethane", 39(25):3674–3676, J Org Chem, 1974.

Ranki et al., "Sandwich hybridization as a convenient method for the detection of nucleic acids in crude samples", 21:77–85, Gene, 1983.

Ransford et al., "2'–O–Ethyl Pyrimidine Nucleosides (1)", 1(3):275–278, J Carbohydrates Nucls Nuclt, 1974.

Rottman et al., "Influence of 2'–O–Alkylation on the Structure of Single–Stranded Polynucleotides and the Stability of 2'–O–Alkylated Polynucleotide Complexes", 13(13):2762–2771, Biochem, 1974.

Shibahara et al., "Site–directed cleavage of RNA", 15(11):4403–4415, Nuc Acids Res, 1987.

Singer et al., "Alkylation of Ribose in RNA Reacted with Ethylinitrosourea at Neutrality", 15(23):5052–5057, Biochem, 1976.

Smrt et al., "Oligonucleotidic Compounds. I. The Direct Blocking of 2'Hydroxyl in Ribonucleoside–3' Phosphates. The Synthesis of 6–Azauridylyl–(5'–>3')–Uridine", 27:73–86, Collect Czech Chem Commun, 1962.

Smrt et al., "Oligonucleotidic Compounds. XIII. 2'–O–(1–Ethoxyethyl)–5'O–Acetylderivatives of Uridine 3' Phosphate and N–Acetylcytidine 3'–Phosphate", 31:2978–2984, Collect Czech Chem Commun, 1966.

Stawinski et al., "Studies on the t–butyldimethylsilyl group as 2'–O–protection in oligoribonucleotide synthesis via the H–phosphonate approach", 16(19):9285–9298, Nuc Acids Res, 1988.

Stein et al., "Oligodeoxynucleotides as Inhibitors of Gene Expression: A Review", 48:2659–2668, Cancer Res, 1988.

Stein et al., "Phosphorotioate and normal oligodeoxyribonucleotides with 5'–linked acridine: characterization and preliminary kinetics of cellular uptake", 72:333–341, Gene, 1988.

Strobel et al., "Double–Strand Cleavage of Genomic DNA at a Single Site by Triple–Helix Formation", 110:7927–7929, J Am Chem Soc, 1988.

Tazawa et al., "A Novel Procedure for the Synthesis of 2'–O–Alkyl Nucleotides", 11(26):4931–4937, Biochem, 1972.

Telser et al., "DNA Oligomers and Duplexes Containing a Covalently Attached Derivative of Tris(2,2'–bipyridine)ruthenium(II): Synthesis and Characterization by Thermodynamic and Optical Spectroscopic Measurements", 111:7221–7226, J Am Chem Soc, 1989.

Telser et al., "DNA Duplexes Covalently Labeled at Two Sites: Synthesis and Characterization by Steady–State and Time–Resolved Optical Spectroscopies", 111:7226–7232, J Am Chem Soc, 1989.

Torrence et al., "Unexpected Conformational Stability of Poly(2'–azido–2'deoxyuridylic acid)", 94(10):3638–3639, J Am Chem Soc, May 17, 1972.

Wallace et al., "The use of synthetic oligonucleotides as hybridization probes. II. Hybridization of oligonucleotides of mixed sequence to rabbit beta–globin DNA", 9(4):879–894, Nuc Acids Res, 1981.

Wetmur et al., "Kinetics of Renaturation of DNA", 31:349–370, J Mol Biol, 1968.

Zon G., "Oligonucleotide Analogues as Potential Chemotherapeutic Agents", 5:539–549, Pharm Res, 1988.

van der Krol et al., "Modulation of Eukaryotic Gene Expression by Complementary RNA or DNA Sequences", 6:958–976, Biotechniques, 1988.

* cited by examiner

2' MODIFIED OLIGONUCLEOTIDES

This application is a continuation of application number U.S. Ser. No. 08/467,422 filed Jun. 6, 1995, now U.S. Pat. No. 5,792,847, which is a continuation of U.S. Ser. No. 08/240,508, filed May 10, 1994, now U.S. Pat. No. B1 5,466,786, which is a continuation of U.S. Ser. No. 07/425,857 filed Oct. 24, 1989, abandoned. U.S. Ser. No. 08/467,422 is incorporated herein by reference.

TECHNICAL FIELD

The invention relates to modified oligonucleotides useful in technologies which rely on complementarity or specificity of oligomer sequences for drug delivery or for direct interference with nucleic acid activity. More specifically, the invention concerns oligomers derivatized at the 2' position, which are stable to nuclease activity.

BACKGROUND ART

There has been considerable activity in recent years concerning the design of nucleic acids as diagnostic and therapeutic tools. One aspect of this design relies on the specific attraction of certain oligomer sequences for nucleic acid materials in vivo which mediate disease or tumors. This general approach has often been referred to as "anti-sense" technology. An oversimplified statement of the general premise is that the administered oligomer is complementary to the DNA or RNA which is associated with, and critical to, the propagation of an infectious organism or a cellular condition such as malignancy. The premise is that the complementarity will permit binding of the oligomer to the target nucleic acid, thus inactivating it from whatever its ordinary function might have been.

A simple illustration would be the administration of a DNA oligomer complementary to an mRNA which encodes a protein necessary to the progress of infection. This administered DNA would inactivate the translation of the mRNA and thus prevent the formation of the protein. Presumably the DNA could be directly administered, or could be used to generate an mRNA complement to the target mRNA in situ. There is by now extensive literature concerned with this general approach, and the methods of utilizing oligomers of this type which are complementary to target RNA or DNA sequences are set forth, for example, in van der Krol, A. R., et al., *Biotechniques* (1988) 6:958–976; Stein, C. A., et al., *Cancer Research* (1988) 48:2659–2668; Izant, J. G., et al., *Science* (1985) 229:345–352; and Zon, G., *Pharmaceutical Research* (1988) 5:539–549, all incorporated herein by reference. In addition, a bibliography of citations relating to anti-sense oligonucleotides has been prepared by Dr. Leo Lee at the Frederick Cancer Research Facility in Frederick, Md.

There are two conceptual additions to the general idea of using complementarity to interfere with nucleic acid functionality in vitro. The first of these is that strict complementarity in the classical base-pairing sense can be supplemented by the specific ability of certain oligonucleotide sequences to recognize and bind sequences in double-helical DNA and to insert itself into the major groove of this complex. A fairly recent but reasonably definitive series of papers has elucidated the current rules for such specificity. These papers take account of very early work by, for example, Arnott, S., et al., *J Mol Biol* (1974) 88:509–521, which indicates the general principle of binding as triplexes poly-dT/poly-dA/poly-dT, and the corresponding analogous triplex involving poly-dC as summarized by Moser, H. E., et al., *Science* (1987) 238:645–650. More recent studies show that the earlier rule (which was that recognition could be achieved by a homopyrimidine oligomer to homopurine/homopyrimidine stretches in the duplex) could be extended to patterns whereby mixed sequences can also be recognized (Griffin, L. C., et al., *Science* (1989) 245:907–971. Further summaries of these phenomena are given, for example, in a review article by Maher III, L. J., et al., *Science* (1989) 245:725–730. Additional related disclosures of triple-helix formation are those by Cooney, M., et al., *Science* (1988) 241:456–459; Francois, J.-C., *Nucleic Acids Res* (1988) 16:11431–11440; and Strobel, S. A., et al., *J Am Chem Soc* (1988) 110:7927–7929. While further details are needed to provide exact sequence specificity studies in this context, it is clear that the rules for "complementarity" in this sense of specific embedding into the major groove of the double-helix are rapidly emerging.

The second aspect of anti-sense technology which deviates from the simple concept of base-pair complementarity in native oligonucleotides results from the early recognition that oligonucleotides, especially RNAs, are highly susceptible to nuclease cleavage in biological systems. In order for these materials to remain active drugs, it would be necessary to stabilize the administered oligonucleotides against this degradation. The approach that has so far been used has been to modify the phosphodiester linkages so as to be resistant to attack by these enzymes. In particular, the phosphodiester linkage has been replaced by phosphoramidate linkages, methylphosphonate linkages, and phosphorothioate linkages. These approaches have certain results with regard to stereoisomerism and its associated impact on hybridization to the target sequences that make them less than completely satisfactory. An alternate approach has been to modify the nucleosides by using 2'-O-methyl ribose or the alpha-anomers of the conventional nucleoside residues. In addition, oligomers containing 2' amino groups have been prepared via their triphosphate analogs and enzyme-catalyzed polymerization by Hobbs, J., et al., *Biochemistry* (1973) 12:5138–5145. Some of these approaches have been summarized in the Zon review cited in the previous paragraph.

The present invention provides additional 2'-substituted pentose moieties for inclusion in the oligomers useful in this technology which are resistant to nuclease activity, and may optionally be combined with additional modifications such as those set forth above.

DISCLOSURE OF THE INVENTION

The invention is directed to nucleosides and nucleotides of the formula:

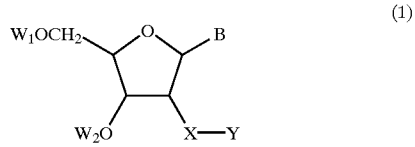

(1)

wherein
B is a purine or pyrimidine residue or analog thereof;
$W_1$ is H, $(PO_3)_m^{-2}$ wherein m is an integer of 1–3; a protecting group, or a group reactive to link hydroxyl groups;
$W_2$ is H, $PO_3^{-2}$, a protecting group, or a group reactive to link hydroxyl groups;
X is O, S, NR or $CR_2$ wherein each R is independently H or alkyl (1–6 C);

Y is a linker moiety, a drug residue optionally attached through a linker moiety, a label optionally attached through a linker moiety, or a property-affecting residue optionally attached through a linker moiety, wherein said X—Y substituent renders an oligomer in which said nucleoside or nucleotide of formula (1) is included more stable to treatment with nuclease than said oligomer which incorporates a corresponding nucleotide having —$H_2$ or —HOH at the 2-position.

These materials are useful as intermediates in the synthesis of the oligomers of the invention, which are oligomers of the formula:

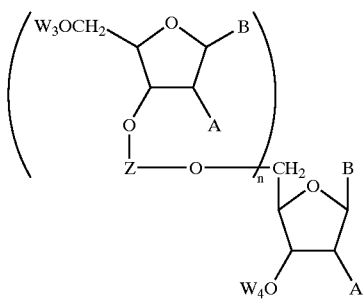

(2)

wherein each B is independently a purine or pyrimidine residue or analog thereof;

$W_3$ and $W_4$ are each independently H, $PO_3^{-2}$, a protecting group, or a group reactive to link hydroxyl groups;

n is an integer of 1–200;

each Z is independently a nucleotide linking residue covalently conjugating the hydroxyl groups of sequential nucleotide residues;

each A is independently selected from the group consisting of H, OH, OH derivatized to a protecting group, and X—Y wherein X is O, S, NR, or $CR_2$ wherein each R is independently H or alkyl (1–6 C); and Y is a linker moiety, a drug residue optionally attached through a linker moiety, a label optionally attached through a linker moiety, or a property-affecting group optionally attached through a linker moiety;

wherein at least one A is X—Y; and wherein the oligomer is more stable to nuclease than the Corresponding oligomer wherein all A are H or OH.

The oligomeric materials of formula (2) are useful as therapeutic or prophylactic agents in protocols which are directed against infectious disease or malignancy by targeting specific DNA and/or RNA sequences associated with the condition, as well as in diagnostic applications.

MODES OF CARRYING OUT THE INVENTION

A. Definitions

The oligomers of the invention contain the residue of at least one nucleotide of formula (1). In this formula, and in the oligomers, B represents a conventional purine or pyrimidine base such as adenine (A), thymine (T), cytosine (C), guanine (G), or uracil (U) or protected forms thereof. Suitable protecting groups include acyl, isobutyryl, benzoyl, and the like. B can, however, also represent a modified or protected form or related derivative of these conventionally occurring bases, i.e., an "analog." A wide range of these analogous heterocyclic bases is known in the art. For example, commonly encountered among such analogs are those which include: 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thioridine, 5-carboxymethylaminomethyluracil, dihydrouracil, beta-D-galactosylqueosine, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), wybutoxosine, pseudouracil, queosine, 2-thiocytosine, 5-methyl-2-thiouracil, 2-thiouracil, 3-(3-amino-3-N-2-carboxypropyl)uracil, (acp3)w, and 2,6-diaminopurine.

As the modification of these bases affects both the stability of the resulting oligomer and the hybridization ability of the sequence, in many instances only a limited number of such substitutions in a particular oligomer is desirable. However, there are other instances when an entire oligomer may be composed of nucleotide residues containing an analog. For example, DNA polymers of uridine and oligomers of 5-bromouridine, and 5-methyl cytidine have been shown to be therapeutically and diagnostically useful. As will be apparent to practitioners of the art, a sensible approach must be used in designing oligomers containing either conventional or modified base forms so that the properties of the resulting monomer are in the desired range. Therefore, in some cases, less than 10% of the bases indicated as "B" in the sequence of formula (2) will be replaced by analogous bases, preferably less than 5%, more preferably less than 1%, and most preferably none at all. However, in other cases, complete replacement by analogs is desirable.

Similar comments apply to the substitution for the bases of nonfunctional substituents such as alkyl or aryl nonheterocyclic groups; however, such substitutions may be permissible to a highly limited extent, for example one residue per 20 or so without actually destroying the functionality of the oligomer. It does not appear there is any particular advantage in making these replacements, and they are permissible only because the replacement may be overwhelmed by the functionality of the remainder of the molecule.

Substituents designated $W_1$–$W_4$ may be H, $PO_3^{-2}$, $(PO_3)_m^{-2}$, protecting groups, or groups reactive to link hydroxyl group.

A "protecting group" in the context of W is a substituent which prevents the reactivity of the —OH to which it is bound in a chemical reaction, typically a reaction to link sequential nucleotides, and which can be removed when the reaction is completed. Typical protecting groups in the compounds of the invention include 4,4'-dimethoxy trityl (DMT), 4-monomethoxytrityl and trityl.

A "group reactive to link hydroxyls" is an intermediate residue in the formation of an internucleotide link between the 5' and 3' hydroxyls. Thus, the reaction of said group with the appropriate —OH of the adjacent nucleotide results in the nucleotide linking residue, Z.

The linking residue represented by Z is typically P(O)O⁻ in naturally occurring oligonucleotides, but can also be P(O)S, P(O)NR$_2$, P(O)R, or P(O)OR', or can be CO or CNR$_2$ wherein R is H or alkyl (1–6C) and R' is alkyl (1–6C) or can be —CX$_2$— wherein each X is independently an electron-withdrawing substituent as described in copending application attorney docket 4610-0005, filed on even date herewith, assigned to the same assignee and incorporated herein by reference. In general, Z can be any nucleotide linking moiety conventionally used to conjugate nucleotide residues to form oligonucleotides.

A linker moiety, as represented by Y (Y' when covalently bound to an additional substituent), is any bivalent bridging residue used to attach a desired substituent to the monomer or oligomer. The linker may be simply binding methylene groups—i.e., —(CH$_2$)$_n$— or may include heteroatoms and functional groups, e.g., —CH$_2$OCH$_2$CH$_2$O— or —CH$_2$O—CH$_2$CH$_2$NH— or —COOCH$_2$CH$_2$O—. The linker residue may also be a residue derived from a commercially available bifunctional linker such as the hetero- and homo-bifunctional linkers marketed by Pierce Chemical Co., Rockford, Ill.

A "drug residue," represented by Y, is the attached portion of a drug useful in conjunction with the oligomer, such as a drug capable of intercalation or of insertion into the minor groove of a DNA-DNA or DNA-RNA double helix or which can effect oligonucleotide cleavage. Examples of such drugs are set forth hereinbelow.

A "label residue" is the attached portion of a label such as a moiety containing a radioisotope, a fluorophore, a chromophore, an enzyme and the like. Such labels may be desirable if this oligomer is to be used in diagnosis.

A "property-affecting" residue is a residue which, by virtue of its presence, results in changed properties of the oligomer. Such changed properties include, but are not limited to, enhancement of cell permeation properties, enhancement of the ability of the oligomer to hybridize to or otherwise bind to oligonucleotide sequences and enhancement of stability to nucleases.

Compounds of the invention that contain groups which are negatively charged at neutral pH can be prepared as their salts. The salts are formed from inorganic bases, such as NaOH, KOH or Ca(OH)$_2$, or organic bases, such as caffeine, various alkylamines, TEA, and DBU.

Compounds of the invention that contain groups which are positively charged at neutral pH can be prepared as acid-addition salts formed from inorganic acids such as HCl, H$_2$SO$_4$ or H$_3$SO$_4$, or from organic acids such as acetic, succinic or citric.

Thus, the nucleotides and their corresponding oligonucleotides may exist as salts depending on the pH at which they find themselves or at which they are prepared. The phosphate and phosphodiester moieties associated with these molecules permits the formation of basic salts such as those formed from inorganic ions such as sodium, potassium, ammonium ions, but especially divalent ions such as calcium and magnesium ions. It is possible, but less common, to form salts of these materials with organic bases such as organic amines or heterocycles.

The invention compounds differ from those of the prior art by having in the 2' position, at either chirality, a substituent which confers nuclease stability and, optionally, provides the capacity to deliver a drug, for example, a reagent which is effective to interact with duplex DNA in its minor groove, provides a label, or provides some additional property. While the remainder of the molecule in formula (2) is sometimes shown for convenience as having the features of the native oligonucleotides, and, indeed, this is often the most preferred embodiment, also included within the invention are molecules which contain the 2' extensions and substitutions of the invention, but also contain additional modifications such as replacement of one or more of the phosphodiester linkages with, for example, a phosphorothioate or methyl phosphonate linkage; a phosphoramidate linkage, including those containing organic amino substituents, such as morpholidates, replacement of all beta-anomers by the alpha-anomer, and the presence or absence of protecting groups or phosphate residues at the 5'- and 3'-termini.

At the 2' position, the invention discloses several general categories of substituents, which share a common type of linkage to the 2' carbon through a substituent selected from O, S, R and CR$_2$, wherein each R is independently selected. In all embodiments, X—Y represents a substituent which is capable, by virtue of its presence, of inhibiting the cleavage of the oligomer in which it is included by nucleases. All of the oligomers of the invention are relatively stable to nucleases.

The stability of the oligomers to nucleases can be determined using any convenient assay, but is conveniently assessed using the snake venom assay illustrated hereinbelow. This assay is conducted as follows: The assay buffer is 0.5 M Tris HCl, pH 8.0, containing 100 µM/MgCl$_2$. Commercially available phosphodiesterase isolated from *Croatalus durissus* is obtained from Boehringer Mannheim as a 50% (v/v) solution in glycerol, pH 6, with a specific activity of approximately 1.2 U/mg. One ul of the phosphodiesterase-containing solution is added to 100 ul buffer, and oligomers are tested by reconstituting 0.15 OD of oligomer in the 100 ul buffer/venom prepared above. Degradation is monitored by observing the disappearance of the 260 nm absorption of the oligomer at its characteristic retention time on HPLC, and measuring the appearance of degradation products.

The oligomers of the invention which contain at least one nucleotide residue containing the 2' substituent are more stable to nuclease as judged by the foregoing assay than the corresponding oligomer containing an unsubstituted 2' position in place of the substituted positions in the invention compounds. By comparing the rate of hydrolysis in the snake venom assay with the invention compound, with that of the corresponding oligomer which is not derivatized in the 2' position, it can be assessed whether the presence of the 2' substituent(s) stabilized the oligomer to cleavage by nucleases.

Typical embodiments of Y, when its sole function is to alter the properties of the oligomer, include alkyl or alkenyl (2–20C), preferably 2–6C, which may or may not be substituted with noninterfering substituents, such as —OH, =O, carboxyl, halo, amino groups and the like, aryl or substituted aryl (6–20C), various alkyl silyl derivatives of the formula SiR$_3$ (wherein each R is alkyl of 2–6C), and similar substituents which also contain heteroatoms. If Y includes a linker moiety, this portion of Y (Y') will provide functional group(s) for conjugation to additional substances. For example, an embodiment of Y' of 1–20C may contain a hydroxyl, amino, mercaptyl, carboxy, keto, or other functional group or several of these in combination. Typical examples include —CH$_2$COOH; —CH$_2$CONH$_2$; —CH$_2$COOEt; —CH$_2$CONHCH$_2$CH$_2$NH$_2$; and the like.

The linker moiety may be utilized to couple the nucleoside, nucleotide or residue within the oligomer to a reagent or drug, such as a drug which is known to interact with the minor groove of duplex DNA or DNA/RNA. A wide variety of these reagents and substances is known and the function, in vivo, is generally to inactivate the DNA duplex with which these reagents interact. Typical examples of such agents include netropsin and its derivatives, anthramycin, quinoxaline antibiotics, actinomycin, pyrrolo (1–4) benzodiazepine derivatives and intercalating agents.

Other drugs, besides those which seek the minor groove, may also be used. Intercalators, toxins, degradation inducers, and the like can also be used. Furthermore, the drug need not be linked through the linker moiety, but may be directly associated with the substituent X, depending on the chemistry of the particular drug.

Another embodiment of Y represents label optionally linked to X through a linker moiety, but also possibly directly attached, again depending on the chemistry in the particular case. Suitable labels include radioisotopes, fluorescent labels, such as fluoroscein and dansyl, chromophores, enzymes and the like. A wide variety of labels is known and can be used to provide detectability when the oligomers of the invention are used as probes or in other specific binding diagnostic assays.

Finally, Y can be a substituent which confers altered properties on the oligomer. It has already been noted that all of the substituents, including drugs and label, confer increased nuclease stability. However, additional properties may also be affected—for example, agents which cleave associated nucleotide chains may be attached; cell permeation enhancement may occur by virtue of the substituent, or Y may enhance the hybridization of the oligomer to complementary oligonucleotides or to a DNA/DNA or DNA/RNA helix. As with all of the foregoing embodiments of Y, the activity or property-changing substituent may be directly bound to X or may be conjugated through a linker moiety.

B. Preparation of the Invention Compounds

Some of the compounds of the invention which are nucleosides or nucleotides are prepared by reacting the corresponding nucleotide or nucleoside having OH in the 2' position with suitable reagents to effect conversion to the substituted form. In some cases, the 2' substituent may be derived from cyclic forms of the nucleoside or nucleotide. Further conversions may be required, as illustrated below, to activate the nucleotide or nucleoside for inclusion into the oligomer. The techniques for these conversions are generally understood in the art, as are the techniques for sequential synthesis of the oligomers.

In particular, dimers may be synthesized to evaluate the effect of the 2' substituent on nuclease activity. In the formation of the dimer, the converted nucleoside or nucleotide of the invention, protected at the 5' position and containing a group reactive to link hydroxyl groups at the 3' position, is reacted with, for example, thymidine or cytidine linked at the 3' position to solid support and the resulting dimer is cleaved from the support and deprotected.

In all of the foregoing cases, conversions to change the functionality and character of the 2' substituent can be conducted either at the monomer or oligomer level. Thus, a 2' substituent which has the formula for X—Y $OCH_2COOEt$ can be converted to an embodiment wherein the substituent is the free acid or the amide either when the ester is a substituent of the single nucleoside or nucleotide, of a dimer, or contained in the oligomeric chain.

The compounds of the invention which are oligomers are obtained by inclusion of the derivatized nucleotide or nucleoside into the oligomer using standard solid phase oligonucleotide synthesis techniques. Such techniques are commercially available for formation of both standard phosphodiester linkages and the conventional substitute linkages described above.

C. Utility and Administration

The compounds of the invention are useful in a manner known in the art for nuclease-inhibited, specifically complementary or binding, oligomers. As set forth above, the general methods for utilization of these compounds are known, and their application to specific diseases or conditions depends on the ascertainment of the appropriate binding specificity. The determination of this binding specificity does not affect the manner of preparation or application of the modified compounds of the invention.

Accordingly, the modified oligomers of the invention are useful in therapeutic, diagnostic and research contexts. In therapeutic applications, the oligomers are utilized in a manner appropriate for antisense therapy in general—as described above, antisense therapy as used herein includes targeting a specific DNA or RNA sequence through complementarity or through any other specific binding means, for example, sequence-specific orientation in the major groove of the DNA double-helix, or any other specific binding mode. For such therapy, the oligomers of the invention can be formulated for a variety of modes of administration, including systemic and topical or localized administration. Techniques and formulations generally may be found in *Remington's Pharmaceutical Sciences,* Mack Publishing Co., Easton, Pa., latest edition.

For systemic administration, injection is preferred, including intramuscular, intravenous, intraperitoneal, and subcutaneous. For injection, the oligomers of the invention are formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays, for example, or using suppositories. For oral administration, the oligomers are formulated into conventional oral administration forms such as capsules, tablets, and tonics.

For topical administration, the oligomers of the invention are formulated into ointments, salves, gels, or creams, as is generally known in the art.

In addition to use in therapy, the oligomers of the invention may be used as diagnostic reagents to detect the presence or absence of the target DNA or RNA sequences to which they specifically bind. Such diagnostic tests are conducted by hybridization through base complementarity or triple helix formation which is then detected by conventional means. For example, the oligomers may be labeled using radioactive, fluorescent, or chromogenic labels and the presence of label bound to solid support detected. Alternatively, the presence of a double or triple helix may be detected by antibodies which specifically recognize these forms. Means for conducting assays using such oligomers as probes are generally known.

In addition to the foregoing uses, the ability of the oligomers to inhibit gene expression can be verified in in vitro systems by measuring the levels of expression in recombinant systems.

It may be commented that the mechanism by which the specifically-binding oligomers of the invention interfere with or inhibit the activity of a target RNA or DNA is not always established, and is not a part of the invention. If the oligomer seeks, for example, a target mRNA, translation may be inhibited. In addition, by binding the target, the degradation of the mRNA message may be enhanced, or the further processing of the RNA may be inhibited. By formation of a triple helix, the transcription or replication of the subject DNA may be inhibited; furthermore, reverse transcription of infectious RNA or replication of infectious DNA is interfered with. It is also thought that the immune function may be modulated through physiological mechanisms similar to those induced by double-stranded RNA as exemplified by the "ampligen" system or similar to those used to suppress systemic lupus erythematosus. The oligomers of the invention are characterized by their ability to target specific oligonucleotide sequences regardless of the mechanisms of targeting or the mechanism of the effect thereof.

Finally, it is understood that the oligonucleotide can be derivatized to a variety of moieties which include, intercalators, chelators, lipophilic groups, label, or any other substituent which modifies but does not materially destroy the oligomeric character of the backbone.

The following examples are intended to illustrate but not to limit the invention. In all synthesis reactions, a dry argon atmosphere was used.

EXAMPLE 1

Preparation of Nucleotides and Oligomers (A= NHAc)

2'-N-acetaminouridine was protected at the 5'-position and made reactive at the 3'-position for formation of a phosphodiester linkage conjugating the residues in an oligomer as follows:

2'-N-Acylaminouridine. To 152 mg of 2'-N-acylamino-3', 5'-O-diacyluridine (Verheyden, J. P. H, et al., Org Chem (1971) 36:250–254) (0.411 mmol) in 25 ml of MeOH was added a catalytic amount of KCN. After 15 h, 1.00 g of silica gel was added, and the reaction was concentrated. The powder was added to the top of a 20 mm column of silica gel that had been equilibrated in 5% $H_2O$ in $CH_3CN$. The column was eluted with 5% $H_2O$ in CH3CN using standard flash chromatography conditions (Still, W. C., et al., *J Org Chem* (1978) 43:2923–2925). Isolation and concentration of the product afforded 59.5 mg (50.8% yield) of product.

2'-N-Acylamino-5'-O-(4,4'-dimethoxytrityl)-uridine. To 59.5 mg of 2'-N-acylaminouridine (0.208 mmol) in 2.5 ml of dry pyridine (that was first concentrated from dry pyridine) was added 77.6 mg (0.229 mmol, 1.10 equiv) of 4,4'-dimethoxytritylchloride. The reaction was stirred a room temperature for 15 h and then diluted with 3.0 ml of $H_2O$. The mixture was partitioned between $H_2O$ and $Et_2O$, shaken and separated. The aqueous layer was extracted with $Et_2O$, and the combined organics were washed with 1% aqueous $NaHCO_{31}$ dried ($Na_2SO_4$), filtered, and concentrated. The residue was purified by flash chromatography on a 20 mm column using first one column volume of $CH_2Cl_2$ and then 8% MeOH in $CH_2Cl_2$ as eluants. Isolation and concentration afforded 70.7 mg of product (56.6% yield) as a colorless foam.

2'-N-Acylamino-5'-O-(4,4'-dimethoxytrityl)-uridin-3-yl-hydrogenphosphonatetriethylammonium salt. To a mixture of 132 mg of 1,2,4-triazole (1.91 mmol) and 0.476 ml of anhydrous 4-methylmorpholine (4.33 mmol) in 2.40 ml of dry $CH_2Cl_2$ was added 0.236 ml of a 2.0 M solution of $PCl_3$ in $CH_2Cl_2$ (0.472 mmol). The mixture was then cooled on an ice-water bath for 30 min. To this mixture was added a solution of 70.7 mg of 2'-N-acylamino-5'-O-(4,4'-dimethoxytrityl)-uridine (0.188 mmol, previously concentrated from dry pyridine) in 0.523 ml of dry pyridine, dropwise over several minutes. The reaction was stirred for 20 min and then poured onto 16.8 ml of cold 1 M aqueous triethylammonium bicarbonate (TEAB,pH=9.0). The mixture was rapidly stirred for 15 min and then extracted with 2×17 ml of $CH_2Cl_2$. The combined organics were washed with 11.7 ml of 1 M aqueous TEAB, dried ($Na_2SO_4$), filtered, and concentrated. The residue was purified by flash chromatography on a 20 mm column using one column volume of 1% TEA in $CH_2Cl_2$, then one column volume of 1% TEA and 2.5% MeOH in $CH_2Cl_2$, and then 1% TEA and 10% MeOH in $CH_2Cl_2$. The product was isolated and concentrated. The residue was partitioned between $CH_2Cl_2$ and 1 M aqueous TEAB, shaken and separated. The organic layer was dried ($Na_2SO_4$), filtered and concentrated. The product was concentrated from dry $CH_3CN$ affording 41.9 mg (43.6% yield) of product as a slightly yellow foam.

The resulting title compound is coupled into oligomers using the method of Froehler, B. C., et al., *Nucleic Acids Res* (1986) 14:5399–5407.

EXAMPLE 2

Preparation of Nucleotides and Oligomers

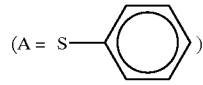

2'-S-phenylcytidine was prepared from 2,2'-anhydro-(1-B-D-arabinofuranosyl) cytosine-HCl (a cyclic nucleoside) by suitable treatment with thiophenol. The $-NH_2$ of cytosine and 5'-hydroxy were protected and the 3'-OH activated as follows:

2'-S-Phenylthiocytidine. To a solution of 500 mg (1.91 mmol) of 2,2'-anhydro-(1-B-D-arabinofuranosyl)-cytosine hydrochloride (purchased from Sigma) in 50 ml of dry DMF and 1.86 ml of dry TEA (13.3 mmol) was added 0.980 ml (9.54 mmol, 5.0 equiv) of thiphenol. The reaction was stirred for 5 h and then concentrated. The residue was concentrated from MeOH onto 2.00 g of silica gel. The powder was added to the top of a 30 mm column of silica gel that was equilibrated with $CH_2Cl_2$. The column was then eluted with one column volume of $CH_2Cl_2$, then one column volume of 6.25% MeOH in $CH_2Cl_2$, then one column volume of 12.5% MeOH in $CH_2Cl_2$, and then 25% MeOH in $CH_2Cl_2$. Concentration of the product fractions afforded 529 mg (82.5% yield) of product as a near colorless oil.

$N^4$-Benzoyl-2'-S-pheylthiocytidine. The method of transient protection (Ti, G. S., et al., *J Am Chem Soc* (1982) 104:1316–1319) was used to prepare the title compound. To 429 mg (1.28 mmol) of 2'-S-phenylthiocytidine (first concentrated from dry pyridine) in 12.2 ml of dry pyridine that was cooled on an ice-water bath was added 0.832 ml (6.56 mmol) of chlorotimethylsilane. The reaction was stirred for 15 min, and then 0.767 ml (6.61 mmol) of benzoyl chloride was added. The ice bath was removed and stirring continued for 2.5 h. The reaction was again cooled on an ice-water bath, and 2.56 ml of $H_2O$ added. The reaction was stirred for 5 min, and then 2.56 ml of concentrated aqueous $NH_4OH$ was added. Stirring was continued for 30 min, and then the mixture was partitioned between EtOAc and $H_2O$, shaken and separated. The aqueous layer was extracted with EtOAc, and the combined organics were washed with $H_2O$, dried ($Na_2SO_4$), filtered, and concentrated. The residue was purified by flash chromatography on a 30 mm column using one column volume of $CH_2Cl_2$ and then 5% MeOH in $CH_2Cl_2$ as eluants. Concentration of the product fractions afforded 138 mg (32.2% yield) of product as an oil.

5'-O-(4,4'-Dimethoxytrityl)-2'-S-phenylthio cytidine. To 138 mg (0.314 mmol) of $N^4$-benzoyl-2'-S-phenylthiocytidine (that was first concentrated from dry pyridine) in 2.00 ml of dry pyridine was added 128 mg (0.377 mmol, 1.2 equiv) of 4,4'-dimethoxytritylchloride. The reaction was stirred for 18 h at room temperature and then diluted with 2.00 ml of $H_2O$. The mixture was partitioned between $Et_2O$ and $H_2O$, shaken and separated. The aqueous layer was extracted with $Et_2O$, and the combined organics washed with 1% aqueous $NaHCO_3$, dried ($Na_2SO_4$), filtered, and concentrated. The crude product was purified by flash chromatography on a 30 mm column using one column volume of $CH_2Cl_2$, then 2.5% MeOH in $CH_2Cl_2$, and then 5% MeOH in $CH_2Cl_2$ as eluants. Concentration of the product fractions afforded 206 mg (88.4% yield) of product.

5'-O-(4,4'-Dimethoxytrityl)-2'-S-phenylthiocytidine-3'-yl-hydrogenphosphonate triethylammonium salt. The preparation of this hydrogenphosphonate was the same as that described above except that 206 mg (0.278 mmol) of 5'-O-(4,4'-dimethoxytrityl)-2'-S-phenylthiocytidine was used, and the reagents were adjusted to the 0.278 mmol scale. After the TEAB workup, the organics were washed with 1 M aqueous TEAB, dried ($Na_2SO_4$), filtered, and concentrated. The residue was purified on a 30 mm column using one column volume of 2% TEA in $CH_2Cl_2$, then 2% TEA and 5% MeOH in $CH_2Cl_2$, and then 2% TEA and 10% MeOH in $CH_2Cl_2$ as eluants. The product fractions were concentrated to a foam which was partitioned between $CH_2Cl_2$ and 1 M aqueous TEAB, shaken, and separated. The organic layer was dried ($Na_2SO_4$), filtered, and concentrated. The product was concentrated from dry $CH_3CN$ affording 165 mg (65.5% yield) of product as a foam.

The resulting title compound is coupled into oligomers using the method of Froehler, B. C., et al., *Nucleic Acids Res* (1986) 14:5399–5407.

EXAMPLE 3

Preparation of Additional Nucleotides and Oligomers

A. (A=$OCH_2COOEt$)

The 2'-derivatized nucleoside was prepared from $N^4$-benzoyl-3',5'-O-(tetraisopropyldisiloxane-1,3-diyl)-cytidine by reaction with ethyl iodoacetate and deprotection of the 2' and 5' hydroxyls. The 5' position was protected and the 3' position converted to a group reactive to link hydroxyl groups.

$N^4$-Benzoyl-2'-O-(ethoxycaronylmethyl)-3',5'-O-(tetraisopropyldisiloxane-1,3-diyl)-cytidine. The preparation of this compound was an adaptation of a similar reaction used for the preparation of the 2'-OMe (Inoue, H., et al., *Nucleic Acids Res* (1987) 15:6131–6149). To 250 mg of $N^4$-benzoyl-3',5'-O-(tetraisopropyldisiloxane-1,3-diyl)-cytidine (Markiewicz, W. J., *J Chem Res* (1979) 181–196) (0.424 mmol; first concentrated from benzene) was added 1.00 ml (8.45 mmol, 19.9 equiv) of ethyl iodoacetate, followed by 294 mg of $Ag_2O$ (1.27 mmol, 2.99 equiv). The mixture was rapidly stirred and heated at 42° C. for 32 h. The mixture was then filtered and concentrated. The residue was taken up in $CH_2Cl_2$, treated with $H_2S$, and concentrated. The dark residue was purified by flash chromatography on a 25 mm column using one column volume of $CH_2Cl_2$, then one column volume of 2.5% MeOH in $CH_2Cl_2$, and the 5% MeOH in $CH_2Cl_2$ as eluants. Concentration of the product fractions afforded 270 mg (94.4% yield) of product as a foam.

$N^4$-Benzoyl-2'-O-(ethoxycarbonylmethyl)-cytidine. To 170 mg of $N^4$-benzoyl-2'-O-(ethoxycarbonylmethyl)-3',5'-O-(tetraisopropyldisiloxane-1,3-diyl)-cytidine (0.252 mmol) in 1.70 ml THF was added 0.126 ml of a 1.0 M solution of tetrabutylammonium fluoride in THF (0.126 mmol, 0.50 equiv). The reaction was stirred at room temperature for 70 min. Then 3.4 ml of pyridine/EtOH/$H_2O$ 3/1/1 (v/v/v) was added and stirring continued for 5 min. Then approximately 10 ml of Amberlyst A-21 ion-exchange resin (pyridinium form) was added and stirring continued for 5 min. The mixture was filtered, and the resin rinsed with EtOH. The combined filtrates were concentrated. The residue was then concentrated from EtOH onto 1.00 g of silica gel. This powder was loaded onto the top of a 25 mm column of silica gel that had been equilibrated with $CH_2Cl_2$. The column was eluted with one column volume of $CH_2Cl_2$, then one column volume of 2.5% MeOH in $CH_2Cl_2$, and then 5% MeOH in $CH_2Cl_2$. Concentration of the product fractions afforded 40.7 mg (37.6% yield) of product as an oil.

$N^4$-Benzoyl-5'-O-(4,4'-dimethoxytrityl)-2'-O-(ethoxycarbonylmethyl)-cytidine. To 40.7 mg of $N^4$-benzoyl-2'-O-(ethoxycarbonylmethyl)-cytidine (0.0939 mmol, first concentrated from dry pyridine) in 1.00 ml dry pyridine was added 38.3 mg of 4,4'-dimethoxytritylchloride (0.113 mmol, 1.2 equiv). The reaction was stirred at room temperature for 20 h and then diluted with 0.50 ml of $H_2O$. The mixture was partitioned between $Et_2O$ and $H_2O$, shaken and separated. The aqueous layer was extracted with $Et_2O$. The combined organics were washed with 1% aqueous $NaHCO_3$, dried ($Na_2SO_4$), filtered, and concentrated. The residue was purified by flash chromatography on a 20 mm column using one column volume $CH_2Cl_2$, then 2.5% MeOH in $CH_2Cl_2$, and then 5.0% MeOH on $CH_2Cl_2$ as eluants. Concentration of the product fractions afforded 55.2 mg (79.9% yield) of product.

$N^4$-Benzoyl-5'-O-(5,5'-dimethoxytrityl)-2'-O-(ethoxycarbonylmethyl)-cytidine-3'-yl-hydrogenphosphonate triethylammonium salt. The preparation of this compound was the same as described in the earlier preparation of hydrogenphosphates except that in this case 55.2 mg (0.0750 mmol) of $N^4$-benzoyl-5'-O-(4,4'-dimethoxytrityl)-2'-O-(ethoxycarbonylmethyl)-cytidine was used, and the reagents adjusted for the 0.0750 mmol scale. After the TEAB workup, the organic layer was washed with 1 M aqueous TEAB, dried ($Na_2SO_4$), filtered, and concentrated. The residue was purified by flash chromatography on a 25 mm column using one column volume of 1% TEA in $CH_3CN$, then one column volume of 1% TEA and 5% $H_2O$ in $CH_3CN$, and then 1% TEA and 10% $H_2O$ in $CH_3CN$. Concentration of the product fractions afforded a foam which was partitioned between $CH_2Cl_2$ and 1 M aqueous TEAB, shaken, and separated. The organics were dried ($Na_2SO_4$), filtered, and concentrated. The product was concentrated from dry $CH_3CN$ affording 23.8 mg (35.2% yield) of product.

The derivatized resulting compound of the previous paragraph was included in an oligomer as described above.

B. (A=OEt)

N4-Benzoyl-2'-O-ethyl-3',5'-O-(tetraisopropyldisiloxane-1,3-diyl)-cytidine was prepared similarly to $N^4$-benzoyl-2'-O-(ethoxycarbonylmethyl)-3',5'-O-(tetraisoproyldisiloxane- 1,3-diyl)-cytidine except that iodoethane was used in place of ethyl iodoacetate. The title compound was then converted to $N^4$-benzoyl-5'-O-(4,4'-dimethoxytrityl)-2'-O-ethyl-cytidine-3'-yl-hydrogenphosphonate triethylammonium salt using the same sequence of steps as for the 2'-O-(ethoxycarbonylmethyl)-compound, and further included in oligomers as described above.

C. (A=OCH$_2$CH$_2$CH$_2$CH$_3$)

$N^4$-Benzoyl-2'-O-butyl-3',5'-O-(tetraisopropyldisiloxane-1,3-diyl)-cytidine was prepared similarly to $N^4$benzoyl-2'-O-(ethoxycarbonylmethyl)-3',5'-O-(tetraisopropyldisiloxane-1,3-diyl)-cytidine except that iodobutane was used in place of ethyl iodoacetate. The title compound was then converted to $N^4$-benzoyl-5'-O-(4,4'-dimethoxytrityl)-2'-O-butyl-cytidine-3'-yl-hydrogenphosphonate triethylammonium salt using the same sequence of steps as for the 2'-O-(ethoxycarbonylmethyl)-compound, and further included in oligomers as described above.

D. (A=O—SiMe2tBu)

5'-O-(4,4'-Dimethoxytrityl)-2'-O-t-butyldimethylsilyluridin-3'-yl-hydrogenphosphonate DBU salt. This compound was prepared differently than described in the literature. The preparation of this compound was the same as for the above compound except that 400 mg (0.606 mmol) of 5'-O-(4,4'-dimethoxytrityl)-2'-O-t-butyldimethylsilyluridine (purchased from Peninsula Labs) was used and the rest of the conditions were scaled to the 0.606 mmol scale. After the TEAB workup, the organic layer was dried (Na$_2$SO$_4$), filtered and concentrated. The residue was purified by flash chromatography on a 35 mm column using one column volume of 1% TEA in CH$_2$Cl$_2$, then one column volume of 1% TEA and 4% MeOH in CH$_2$Cl$_2$, and then 1% TEA and 8% MeOH in CH$_2$Cl$_2$ as eluants. The product was isolated and concentrated. The foam was partitioned between CH$_2$Cl$_2$ and 1 M aqueous 1,8-diazabicyclo[5.4.0]undec-7-ene bicarbonate (DBU bicarbonate, pH=9.0), shaken and separated. The organic layer was again washed with 50 mL of 1 M aqueous DBU bicarbonate, dried (Na$_2$SO$_4$), filtered and concentrated. The product was concentrated from dry CH$_3$CN affording 435 mg (81.9% yield) of product as an oil. The resulting derivative is included in an oligomer synthesized by standard methods.

EXAMPLE 4

Conversion of 2' Substituents in Oligomers

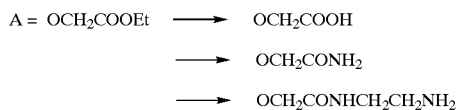

$N^4$-Benzoyl-5'-O-(4,4'-dimethoxytrityl)-2'-O-(ethoxycarbonylmethyl)-cytidin-3'-yl-hydrogenphosphonate triethylammonium salt was coupled into oligonucleotides using the hydrogen phosphonate method.

In order to generate the 2'OCH$_2$CO$_2$H, the oligo was deprotected, cleaved from the support, and the 2'OCH$_2$CO$_2$Et hydrolyzed to the 2'OCH$_2$CO$_2$H using 0.1 M aqueous NaOH at 45° C. for 4.5 h.

In order to generate the 2'OCH$_2$CONH$_2$, the above oligo containing the 2'OCH$_2$CO$_2$Et was deprotected, cleaved from the support and the 2'OCH$_2$CO$_2$Et converted to the 2'OCH$_2$CONH$_2$ using NH$_3$ in MeOH at 45° C. for 29 h.; the corresponding amide of the formula —OCH$_2$CONHCH$_2$CH$_2$NH$_2$ was prepared similarly.

EXAMPLE 5

Resistance to Nuclease Activity of the Compounds of the Invention

The ability of dimers of the compounds synthesized in Example 1 to resist the activity of nucleases was determined. The illustrated compounds of Formula 1 were coupled to an additional unmodified thymidine using standard procedures to obtain compounds of the formula:

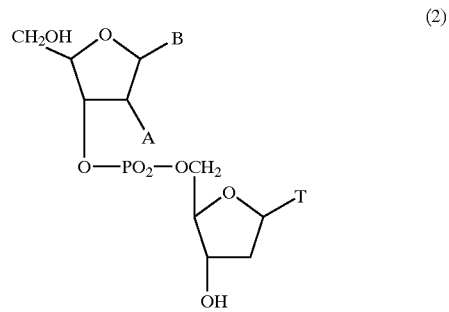

(2)

The resulting dimeric compounds were tested for stability with respect to nuclease from snake venom as described above. The following results are shown in Table 1.

TABLE 1

| —X—Y—Z | Snake Venom | |
|---|---|---|
| | % dimer after 5 min. | Time for 100% degradation |
| —H | 0% | <5 min. |
| —OCH$_3$ | 20% | — |
| —SPh | 75% | >140 min. |
| —OCH$_2$CO$_2$H | 40% | 46 min. |
| —OCH$_2$CONH$_2$ | 51% | >42 min. |
| —OTBS | >99% | >>140 min. (77% dimer after 140 min.) |
| —OCH$_2$CONHCH$_2$CH$_2$NH$_2$ | 100% | >>140 min. (>99% dimer after 140 min. |

As shown in Table 1, the addition of the substituent to the 2'-position greatly enhances the stability of the resulting dimer to nuclease cleavage.

What is claimed is:

1. An oligonucleotide having the formula:

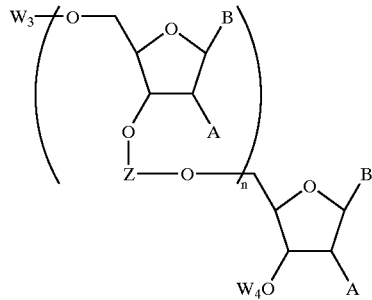

or a salt thereof, wherein:
each B independently is a protected or unprotected purine or pyrimidine base in the β-anomeric configuration;

$W_3$ and $W_4$ are each independently H, $PO_3^{-2}$, a protecting group, or an intermediate moiety in the formation of an internucleotide link which when reacted with the appropriate —OH results in Z;

n is an integer of 1–200;

each Z is independently is P(O)O, P(O)S or P(O)N(R)$_2$ provided at least one Z is not P(O)O;

each R is independently H or alkyl ($C_{1-6}$);

each A is $OCH_3$, H, OH, O—Pr wherein Pr is a protecting group, or X—Y wherein:
X is O; and
Y is substituted or unsubstituted alkyl ($C_{2-20}$) or substituted or unsubstituted alkenyl ($C_{2-20}$), wherein the substituents are a halogen, OH, $NH_2$, SH, —O—, —$CH_2CONH_2$, —$CH_2COOCH_2CH_3$, or $CH_2CONHCH_2NH_2$; and at least one A is $OCH_3$.

2. The oligonucleotide of claim 1 wherein $W_3$ and $W_4$ are H.

3. The oligonucleotide of claim 1 wherein at least one Z is P(O)N(R)$_2$.

4. The oligonucleotide of claim 1 wherein at least one Z is P(O)S.

5. The oligonucleotide of claim 1 wherein at least one A is X—Y.

6. The oligonucleotide of claim 5 wherein Y is substituted alkyl.

* * * * *

UNITED STATES PATENT AND TRADEMARK OFFICE
CERTIFICATE OF CORRECTION

PATENT NO.    : 6,476,205 B1
DATED         : November 5, 2002
INVENTOR(S)   : Chris A. Buhr et al.

It is certified that error appears in the above-identified patent and that said Letters Patent is hereby corrected as shown below:

Title page,
Item [56], References Cited, OTHER PUBLICATIONS, "Singer, et al.," reference, please delete "Ethylinitrosourea" and insert therefor -- Ethylnitrosourea -- ;
"Smrt, et al.,"please insert -- - -- between "2'" and "Hydroxyl" so it appears as -- 2'-Hydroxyl --;
"Smrt, et al.," please insert -- - -- between "3'" and "Phosphate" so it appears as -- 3'-Phosphate --;
"Torrence, et al.," please delete "(2'-azido-2'deoxyuridylic acid)" and insert therefor -- (2'-azido-2'-deoxyuridylic acid) --

Signed and Sealed this

Twenty-second Day of June, 2004

JON W. DUDAS
*Acting Director of the United States Patent and Trademark Office*